(12) United States Patent
Kemp (10) Patent No.: US 11,951,292 B2
(45) Date of Patent: Apr. 9, 2024

(54) AUTOINJECTOR

(71) Applicant: Sanofi-Aventis Deutschland GMBH, Frankfurt am Main (DE)

(72) Inventor: Thomas Kemp, Ashwell (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 809 days.

(21) Appl. No.: 16/777,509

(22) Filed: Jan. 30, 2020

(65) Prior Publication Data
US 2020/0164156 A1 May 28, 2020

Related U.S. Application Data

(63) Continuation of application No. 14/903,390, filed as application No. PCT/EP2014/064423 on Jul. 7, 2014, now Pat. No. 10,583,260.

(30) Foreign Application Priority Data

Jul. 9, 2013 (EP) ..................... 13175660

(51) Int. Cl.
*A61M 5/32* (2006.01)
*A61M 5/20* (2006.01)
*A61M 5/50* (2006.01)

(52) U.S. Cl.
CPC .......... *A61M 5/326* (2013.01); *A61M 5/2033* (2013.01); *A61M 5/3204* (2013.01);
(Continued)

(58) Field of Classification Search
CPC .. A61M 5/3204; A61M 5/2033; A61M 5/326; A61M 5/5086; A61M 2005/2013; A61M 2005/206; A61M 2005/208; A61M 2005/3247; A61M 2205/581; A61M 2205/582; A61M 2205/584; A61M 2005/3267; A61M 5/3257; A61M 5/3243
See application file for complete search history.

(56) References Cited

U.S. PATENT DOCUMENTS

2005/0101919 A1* 5/2005 Brunnberg ............ A61M 5/326
604/197
2010/0010454 A1* 1/2010 Marshall ............... A61M 5/326
604/208
(Continued)

FOREIGN PATENT DOCUMENTS

CN 101983079 3/2011
CN 102770173 11/2012
(Continued)

OTHER PUBLICATIONS

Extended European Search Report in Application No. 13175660.3, dated Jan. 2, 2014, 7 pages.
(Continued)

*Primary Examiner* — James D Ponton
(74) *Attorney, Agent, or Firm* — Fish & Richardson P.C.

(57) ABSTRACT

An autoinjector includes a case, a syringe carrier slidably disposed within the case and adapted to hold a syringe including a stopper, a plunger slidably disposed within the syringe carrier and adapted to apply a force on the stopper, and a drive spring disposed within the plunger and biasing the plunger relative to the syringe carrier.

15 Claims, 8 Drawing Sheets

(52) U.S. Cl.
CPC ............... *A61M 2005/2013* (2013.01); *A61M 2005/206* (2013.01); *A61M 2005/208* (2013.01); *A61M 2005/3247* (2013.01); *A61M 5/5086* (2013.01); *A61M 2205/581* (2013.01); *A61M 2205/582* (2013.01); *A61M 2205/584* (2013.01)

(56) References Cited

U.S. PATENT DOCUMENTS

| | | | |
|---|---|---|---|
| 2010/0298780 A1* | 11/2010 | Laiosa | A61M 5/2033 604/198 |
| 2011/0213314 A1 | 9/2011 | Guillermo | |
| 2012/0209192 A1 | 8/2012 | Alexandersson | |
| 2014/0207106 A1 | 7/2014 | Bechmann et al. | |
| 2014/0330216 A1 | 11/2014 | Weaver | |

FOREIGN PATENT DOCUMENTS

| | | |
|---|---|---|
| CN | 102917742 | 2/2013 |
| EP | 2438942 | 4/2012 |
| EP | 2489380 | 8/2012 |
| EP | 3019217 | 9/2018 |
| JP | 2010-532189 | 10/2010 |
| WO | WO 2009/007229 | 1/2009 |
| WO | WO 2009/063030 | 5/2009 |
| WO | WO 2011/109205 | 9/2011 |
| WO | WO 2011/111006 | 9/2011 |
| WO | WO 2012/045827 | 4/2012 |
| WO | WO 2012/045831 | 4/2012 |
| WO | WO 2013/034984 | 3/2013 |

OTHER PUBLICATIONS

International Preliminary Report on Patentability in International Application No. PCT/EP2014/064423, dated Jan. 12, 2016, 7 pages.

International Search Report and Written Opinion in International Application No. PCT/EP2014/064423, dated Nov. 10, 2014, 10 pages.

Rote Liste, "50. Hypophysen-, Hypothalamushormone, andere regulatorische Peptide u. ihre Hemmstoffe," Chapter 50, ed. 2008, 20 pages.

\* cited by examiner

AUTOINJECTOR

CROSS-REFERENCE TO RELATED APPLICATIONS

This application is a continuation of U.S. patent application Ser. No. 14/903,390, filed Jan. 7, 2016, which is a U.S. national stage application under 35 USC § 371 of International Application No. PCT/EP2014/064423, filed on Jul. 7, 2014, which claims priority to European Patent Application No. 13175660.3, filed on Jul. 9, 2013, the entire contents of which are incorporated herein by reference.

TECHNICAL FIELD

The present disclosure relates to an autoinjector.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

Certain aspects of the present invention provide improved autoinjectors.

In an exemplary embodiment, an autoinjector according to certain aspects of the present invention comprises a case, a syringe carrier slidably disposed within the case and adapted to hold a syringe including a stopper, a plunger slidably disposed within the syringe carrier and adapted to apply a force on the stopper, and a drive spring disposed within the plunger and biasing the plunger relative to the syringe carrier.

In an exemplary embodiment, the autoinjector further comprises a needle shroud slidably disposed within the case. The needle shroud is telescopically arranged over the syringe carrier. In an exemplary embodiment, the autoinjector further comprises detent mechanism adapted to couple the needle shroud to the syringe carrier and adapted to couple the needle shroud to the case. The detent mechanism comprises a resilient shroud beam on the needle shroud having a shroud boss releasably engaging a carrier opening in the syringe carrier. The case includes a proximal case boss abutting the shroud boss when the needle shroud is in a first extended position.

In an exemplary embodiment, the autoinjector further comprises a plunger release mechanism adapted to releasably couple the plunger to the syringe carrier. The plunger release mechanism comprises a resilient carrier beam on the syringe carrier having a carrier boss releasably engaging a plunger opening in the plunger.

In an exemplary embodiment, the autoinjector further comprises a collar slidably arranged on the syringe carrier, and a control spring applying a biasing force to the collar. The collar includes a resilient collar beam having a collar boss adapted to releasably engage a step on the syringe carrier. The collar abuts the carrier boss when the needle shroud is in the first extended position. The collar, the needle shroud and the syringe carrier are moved proximally relative to the case when the needle shroud is moved from the first extended position to a first retracted position. A proximal end of the syringe carrier abuts a proximal end of the case when the needle shroud is in the first retracted position to provide a feedback. The shroud boss is proximal of the proximal case boss when the needle shroud is in the first retracted position. The syringe carrier is advanced distally when the needle shroud is in a second retracted position proximal of the first retracted position, and the shroud boss disengages the carrier opening. When the shroud boss disengages the carrier opening, the collar pushes the syringe carrier distally until the syringe carrier abuts a front stop in the case and the collar disengages the syringe carrier under the biasing force of the control spring and pushes the needle shroud into a second extended position relative to the case. When the collar disengages the syringe carrier, the carrier boss disengages the plunger opening to release the plunger. The shroud boss abuts a distal case boss when the needle shroud is in the second extended position.

In an exemplary embodiment, the syringe carrier with the integrated drive spring allows for employing a strong drive spring without any impact on the user when triggering the autoinjector or during needle insertion since these actions are achieved or opposed by the control spring which can be specified considerably weaker than the drive spring. This allows for delivering highly viscous medicaments.

In an exemplary embodiment, releasing the drive spring upon the needle reaching an insertion depth avoids a so called wet injection, i.e. medicament leaking out of the needle which is a problem in conventional art autoinjectors, where both needle insertion and injection are achieved by pushing on the stopper.

In an exemplary embodiment, the autoinjector has a particularly low part count compared to most conventional autoinjectors thus reducing manufacturing costs. The arrangement with separate control spring for advancing the syringe and the needle shroud and a drive spring for fluid injection allows for using one design for different viscosity liquids by just changing the drive spring, and for different volumes just by changing the length of the plunger. This may be an advantage over conventional designs where the drive spring also serves for needle insertion and/or for advancing a shroud.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present disclosure will become more fully understood from the detailed description given hereinbelow and the accompanying drawings which are given by way of illustration only, and thus, are not limitive of aspects of the present invention, and wherein.

Corresponding parts are marked with the same reference symbols in all figures.

DETAILED DESCRIPTION

Figure 1A:
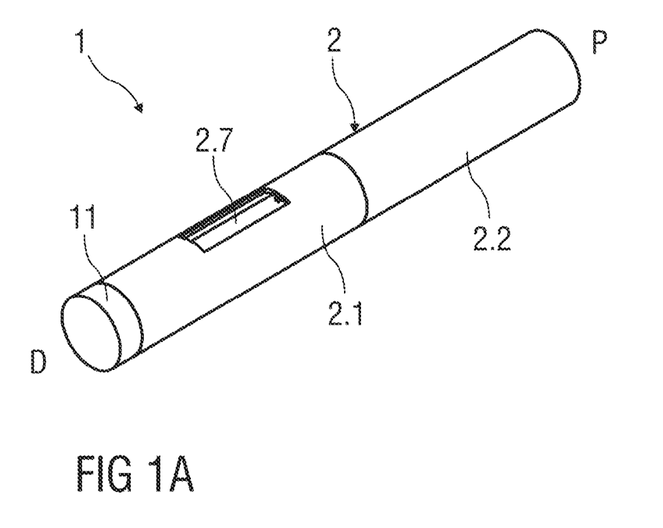
FIG. 1A is a perspective view of an exemplary embodiment of an autoinjector prior to use.
Figure 1B:
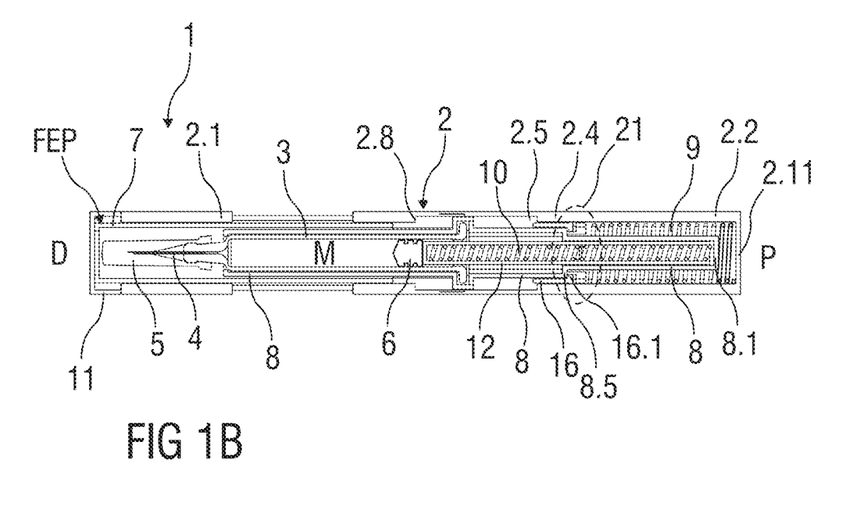
FIG. 1B is a longitudinal section of an exemplary embodiment of an autoinjector prior to use.
Figure 1C:
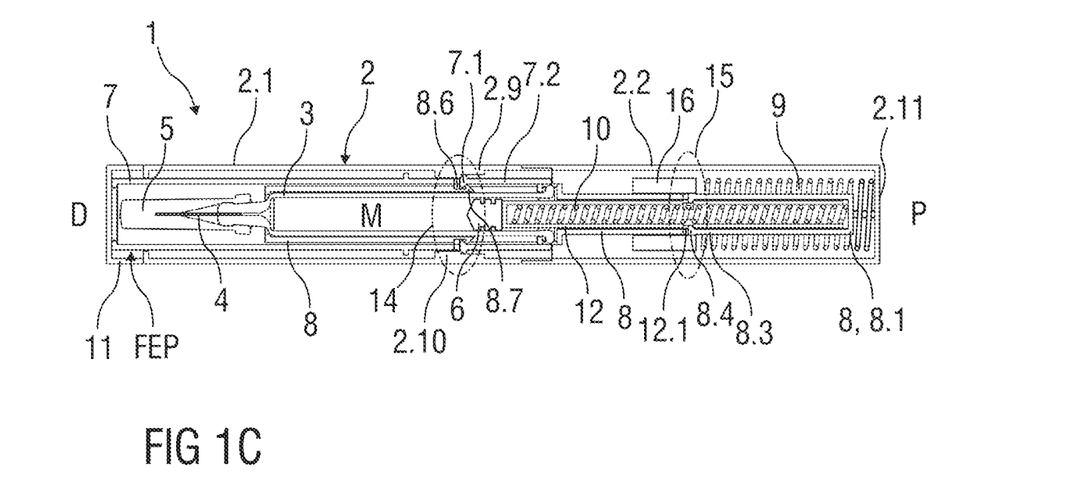
FIG. 1C is a different longitudinal section of an exemplary embodiment of an autoinjector prior to use.

FIG. 1A is a perspective view of an exemplary embodiment of an autoinjector 1 comprising a case 2 and a cap 11 prior to use. FIGS. 1B and 1C are longitudinal sections of the autoinjector 1 prior to use.

In an exemplary embodiment, the autoinjector 1 comprises a case 2 including a distal case 2.1 and a proximal case 2.2 which are coupled during assembly. A cap 11 is removably coupled to a distal end of the case 2. The case 2 comprises a viewing window 2.7, which may be a hole or a transparent portion of the case 2.

The case 2 is adapted to hold a syringe 3 containing a medicament. The syringe 3 may be a pre-filled syringe and have a needle 4 arranged at a distal end. In another exemplary embodiment, the syringe 3 may be a medicament cartridge adapted to removably receive the needle 4 (e.g., by snap-fit, friction, threads, etc.). A protective needle sheath 5 may be removably attached to the needle 4. A stopper 6 is arranged for sealing the syringe 3 proximally and for displacing a liquid medicament M contained in the syringe 3 through the needle 4.

A needle shroud 7 is telescoped within the case 2 and movable between an extended position and a retracted position. The needle shroud 7 is biased relative to the case 2 toward the extended position by a control spring 9.

In an exemplary embodiment, the syringe 3 may be held in a syringe carrier 8, which is slidably arranged within the case 2. The syringe carrier 8 may include a distal portion adapted to hold the syringe 3 and a proximal portion adapted to retain a plunger 12. A drive spring 10, e.g., a compression spring, may be grounded proximally on a proximal end of the syringe carrier 8 and distally on a distal end of the plunger 12. In an exemplary embodiment, the plunger 12 is telescopically coupled to the proximal portion of the syringe carrier 8, and the drive spring 10 is arranged within the plunger 12 and biases the plunger 12 distally.

In an exemplary embodiment, the drive spring 10 is arranged within a proximal part 8.1 of the syringe carrier 8. A plunger 12 serves for forwarding the force of the drive spring 10 to the stopper 6. In an exemplary embodiment the plunger 12 is hollow and telescoped within the proximal part 8.1 of the syringe carrier 8 wherein the drive spring 10 is arranged within the plunger 12 biasing the plunger 12 in the distal direction D against the syringe carrier 8.

In an exemplary embodiment, a detent mechanism 14 is provided to initiate automated needle insertion. The detent mechanism 14 also locks the needle shroud 7 after autoinjector 1 has been removed from the injection site in an extended position.

In an exemplary embodiment, the detent mechanism 14 comprises at least one shroud boss 7.1 adapted to engage in a carrier opening 8.6 within the syringe carrier 8 for locking the needle shroud 7 to the syringe carrier 8. At least one surface of the shroud boss 7.1 and the carrier opening 8.6 may be ramped to reduce a force necessary to displace the needle shroud 7 from the extended position to the retracted position against the biasing force of the control spring 9. When the force on the needle shroud 7 overcomes the biasing force of the control spring 9, the shroud boss 7.1 abuts the carrier opening 8.6 and deflects radailly via a compliant beam 7.2 coupled to the shroud boss 7.1, disengaging the needle shroud 7 from the syringe carrier 8. When the needle shroud 7 is in a first extended position FEP relative to the case 2 (as shown in FIGS. 1B and 1C), the shroud boss 7.1 radially abuts a radial case boss 2.9, which prevents the needle shroud 7 from disengaging the syringe carrier 8 when the needle shroud 7 is in the first extended position FEP. An axial case boss 2.10 is adapted to distally abut the shroud boss 7.1 such that the needle shroud 7 cannot be moved distally beyond the first extended position FEP prior to use. At least one of the surfaces of the shroud boss 7.1 and the axial case boss 2.10 may be ramped such that if an axial force directed in the distal direction D is applied to the needle shroud 7 relative the case 2, the needle shroud 7 moves in the distal direction D relative the case 2 and the shroud boss 7.1 is radially inwardly deflected via the resilient beam 7.2 around the axial case boss 2.10. Prior to use, the shroud boss 7.1 is prevented from deflecting radially inward by the presence of the syringe carrier 8. Thus, prior to use the needle shroud 7.1 does not disengage the case 2.

In an exemplary embodiment, a plunger release mechanism 15 is arranged for preventing release of the plunger 12 prior to the needle 4 reaching an insertion depth and for releasing the plunger 12 once the needle 4 reaches its insertion depth. In an exemplary embodiment, the plunger release mechanism 15 comprises: one or more compliant beams 8.3 with a respective first boss 8.4 arranged on the syringe carrier 8, a respective first opening 12.1 laterally arranged in the plunger 12 for engaging the first boss 8.4, a collar 16 slidably arranged within the case 2 and over the syringe carrier 8. When the needle shroud 7 is in the first extended position FEP, the collar 16 abuts the first boss 8.4, preventing it from disengaging the first opening 12.1. As described further below, as the needle 4 reaches its insertion depth, the collar 16 moves axially away from the first boss 8.4, so that the first boss 8.4 may deflect via the beam 8.3 and disengage from the first opening 12.1. The syringe carrier 8 is then disengaged from the plunger 12. At least surface of the first boss 8.4 and the first opening 12.1 may be ramped to reduce a force necessary to disengage the first boss 8.4 from the first opening 12.1.

In an exemplary embodiment, a control mechanism 21 (shown in FIG. 3B) is arranged for selectively coupling the control spring 9 to the syringe carrier 8 or to the needle shroud 7 for advancing either in the distal direction D or opposing movement thereof in the proximal direction P. In an exemplary embodiment, the collar 16 may be a component of the control mechanism 21. The control spring 9 is proximally grounded in the case 2 and distally bears against the collar 16 which is movable axially with respect to the case 2 and arranged over the syringe carrier 8. The collar 16 comprises at least one collar boss 16.1 adapted to be engaged to a step 8.5 in the carrier 8. At least one of the mating surfaces of the carrier boss 16.1 and the step 8.5 may be ramped to reduce a force necessary to deflect the collar boss 16.1 radially via a compliant collar beam 16.2 when it abuts the step 8.5. Once assembled, the collar boss 16.1 is prevented from deflecting radially by a narrow section 2.4 in the case 2. A wide section 2.5 is arranged distally from the narrow section 2.4. Upon axial movement of the syringe carrier 8 and the collar 16 in the distal direction D, the carrier boss 16.1 can deflect radially when the collar 16 enters the wide section 2.5 and disengage the collar 16 from the syringe carrier 8 under force from the control spring 9.

In an exemplary embodiment, prior to use the control spring 9 is compressed between the case 2 and the collar 16. The control mechanism 21 couples the collar 16 to the syringe carrier 8 which is in turn coupled to the case 2 by the detent mechanism 14.

A exemplary embodiment of a sequence of operation of the autoinjector 1 is as follows:

Prior to use, the autoinjector 1 is in the state as illustrated in FIGS. 1A to 10. If applicable, the user removes the autoinjector 1 from a packaging. The medicament M may be viewed through the viewing window 2.7. The cap 11 is removed from the case 2 by pulling the cap 11 in the distal direction D. The cap 11 is coupled to the protective needle sheath 5, and thus removing the cap 11 also removes the protective needle sheath 5. Prior to use, the needle shroud 7 is in the first extended position FEP protruding from the case 2 in the distal direction D. The first extended position FEP is defined by the detent mechanism 14, i.e. by the engagement of the shroud boss 7.1 in the carrier opening 8.6 of the syringe carrier 8 and abutment of the shroud boss 7.1 against the axial case boss 2.10 to prevent it from disengaging the carrier opening 8.6.

Figure 2A:
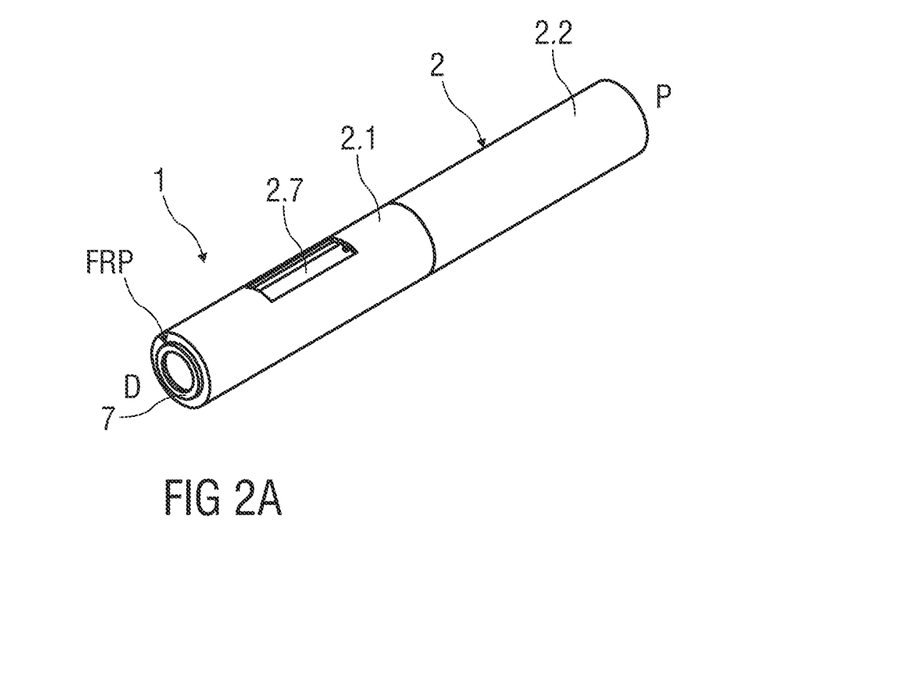
FIG. 2A is a perspective view of an exemplary embodiment of an autoinjector during use.
Figure 2B:
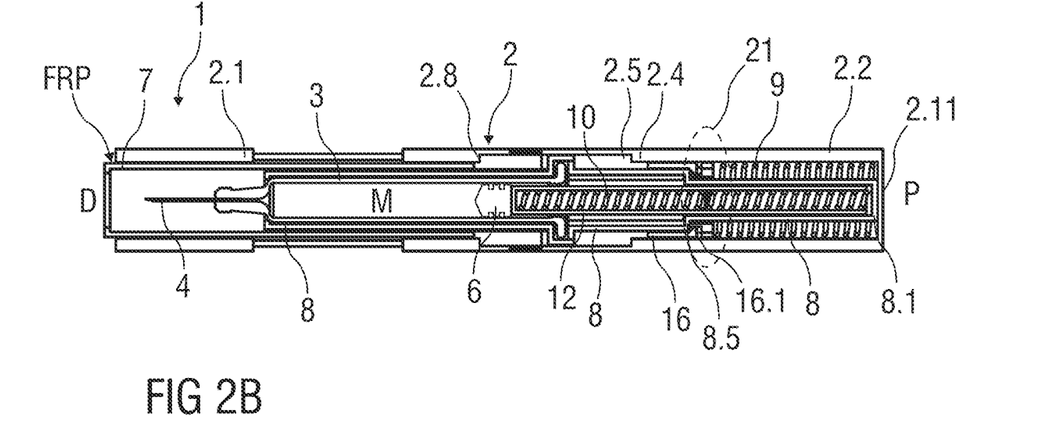
FIG. 2B is a longitudinal section of an exemplary embodiment of an autoinjector during use.
Figure 2C:
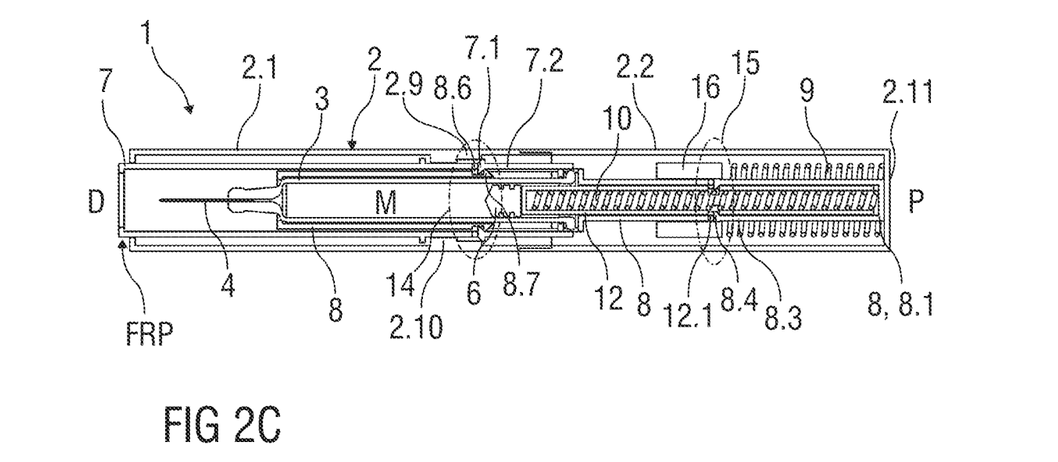
FIG. 2C is a different longitudinal section of an exemplary embodiment of an autoinjector during use.

FIGS. 2A-C are perspective views of the autoinjector 1 being pressed against an injection site. When the autoinjector 1 is pressed against the injection site, the needle shroud 7 moves from the first extended position FEP toward a first retracted position FRP relative to the case 2. Because the needle shroud 7 is coupled to the syringe carrier 8 by the detent mechanism 14 (by the shroud boss 7.1 engagement with the carrier opening 8.6), the syringe carrier 8 (and the syringe 3 therein) are retracted relative to the case 2 such that the needle 4 is not exposed. Because the collar 16 is coupled to the syringe carrier 8 (by the collar boss 16.1 abutting the step 8.5), the collar 16 is moved with the syringe carrier 8 in the proximal direction P against the force of the control spring 9.

When the needle shroud 7 has reached the first retracted position FRP, the proximal end 8.1 of the syringe carrier 8 may contact (or nearly contact) a proximal end 2.11 of the case 2. The contact between the syringe carrier 8 and the case 2 (and/or the increased resistance provided by the control spring 9) may provide a tactile feedback that further depression of the needle shroud 7 will activate the autoinjector 1. In the first retracted position FRP, the shroud boss 7.1 is proximal of the case boss 2.9 such that the shroud boss 7.1 no longer abuts the case boss 2.9. However, in an exemplary embodiment, the biasing force of the control spring 9 is less than the force required to deflect the shroud boss 7.1 out of the carrier opening 8.6. Thus, if the needle shroud 7 is not further depressed and the autoinjector 1 is removed from the injection site (or axial force is no longer applied to the autoinjector 1), the needle shroud 7 will re-extend into the first extended position FEP and the autoinjector 1 will return to its initial state.

Figure 3A:
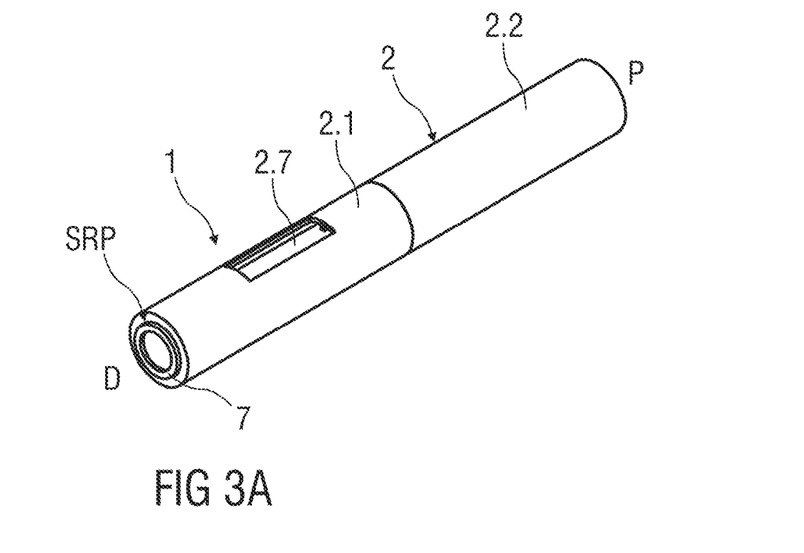
FIG. 3A is a perspective view of an exemplary embodiment of an autoinjector during use.
Figure 3B:
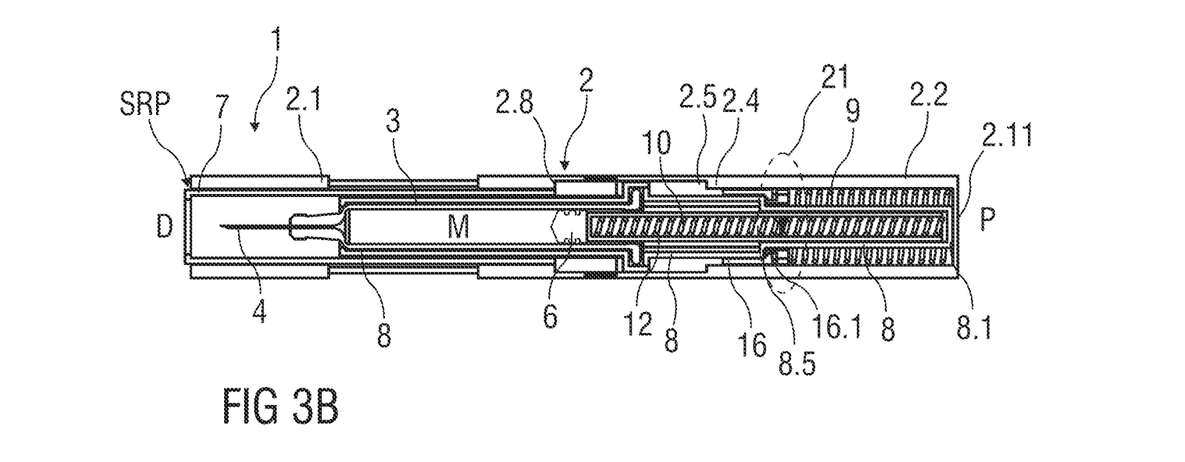
FIG. 3B is a longitudinal section of an exemplary embodiment of an autoinjector during use.
Figure 3C:
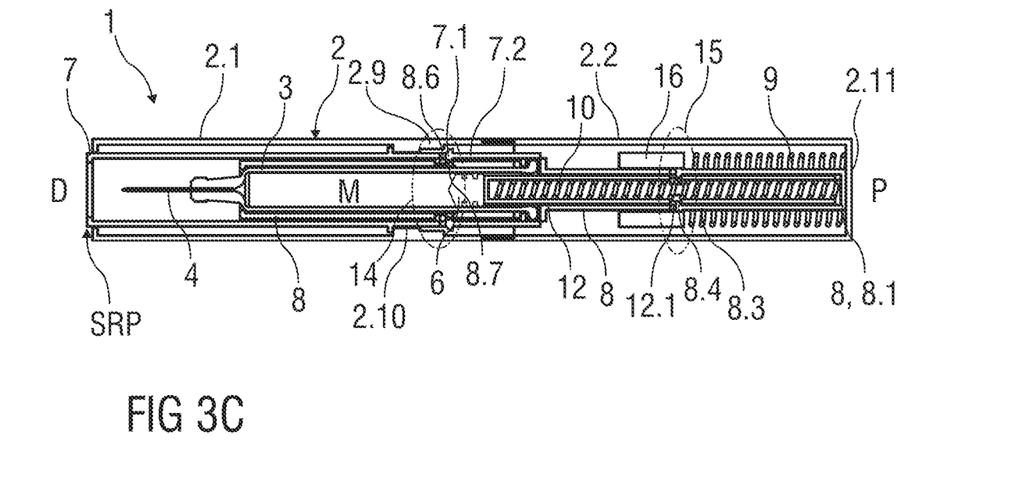
FIG. 3C is a different longitudinal section of an exemplary embodiment of an autoinjector during use.

FIGS. 3A-C are perspective views of the autoinjector 1 being pressed against an injection site. As the user continues to depress the needle shroud 7 into a second retracted position SRP, an increase in resistance is experienced as the case 2 advances the syringe carrier 8 in the distal direction D relative to the needle shroud 7 through contact of the proximal ends 2.11, 8.1 of the case 2 and the syringe carrier 8. As the shroud boss 7.1 is no longer radially supported by the case boss 2.9, as the case 2 is advanced in the distal direction D, the shroud boss 7.1 is deflected radially when it abuts the carrier opening 8.6, causing the syringe carrier 8 to disengage from the needle shroud 7.

Figure 4A:
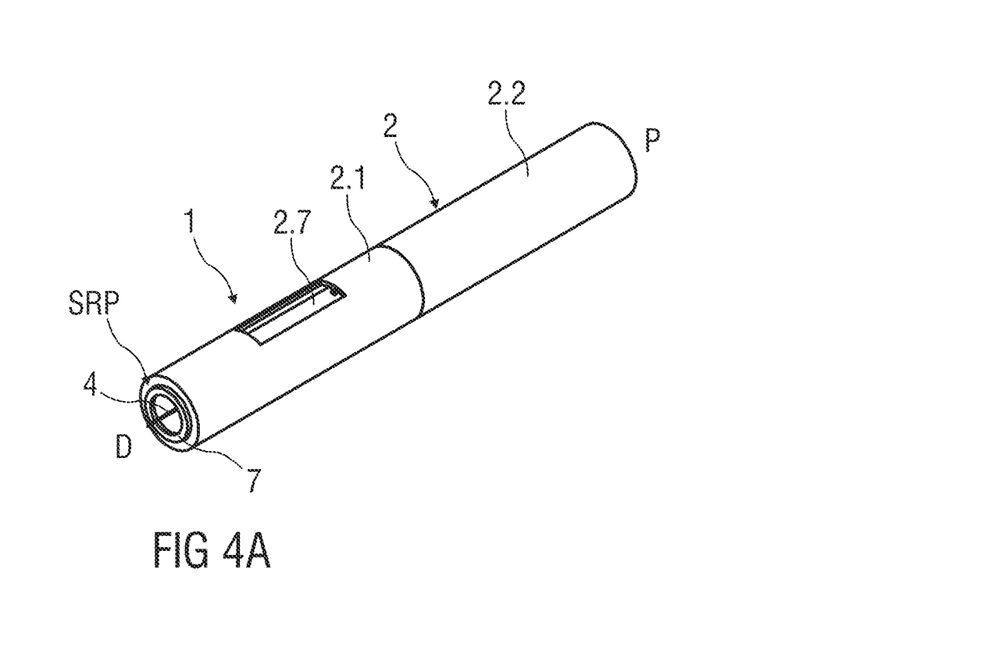
FIG. 4A is a perspective view of an exemplary embodiment of an autoinjector during use.
Figure 4B:
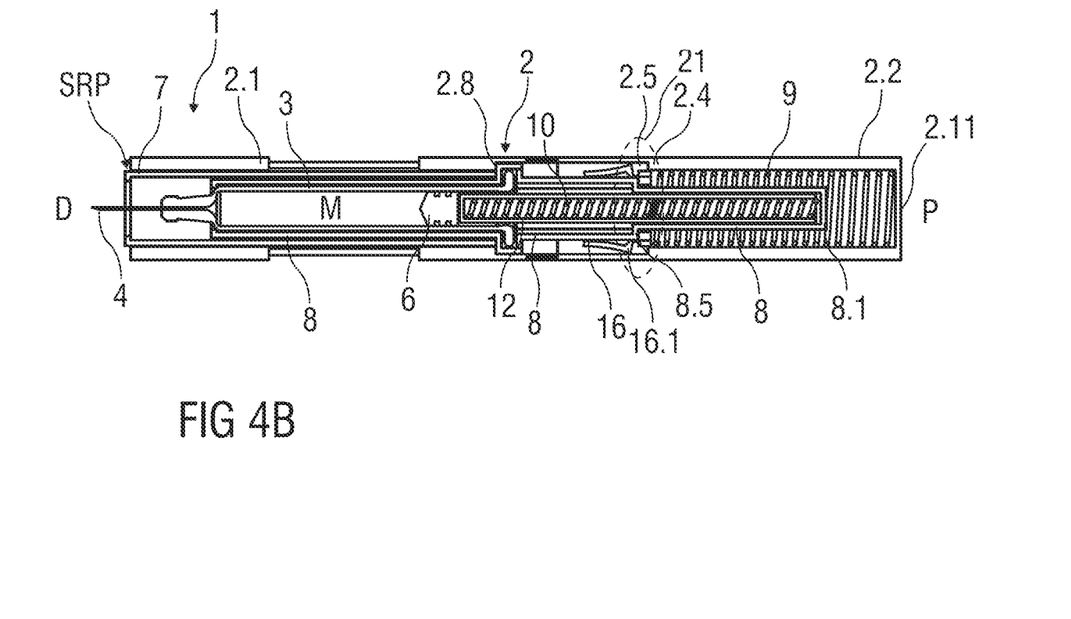
FIG. 4B is a longitudinal section of an exemplary embodiment of an autoinjector during use.
Figure 4C:
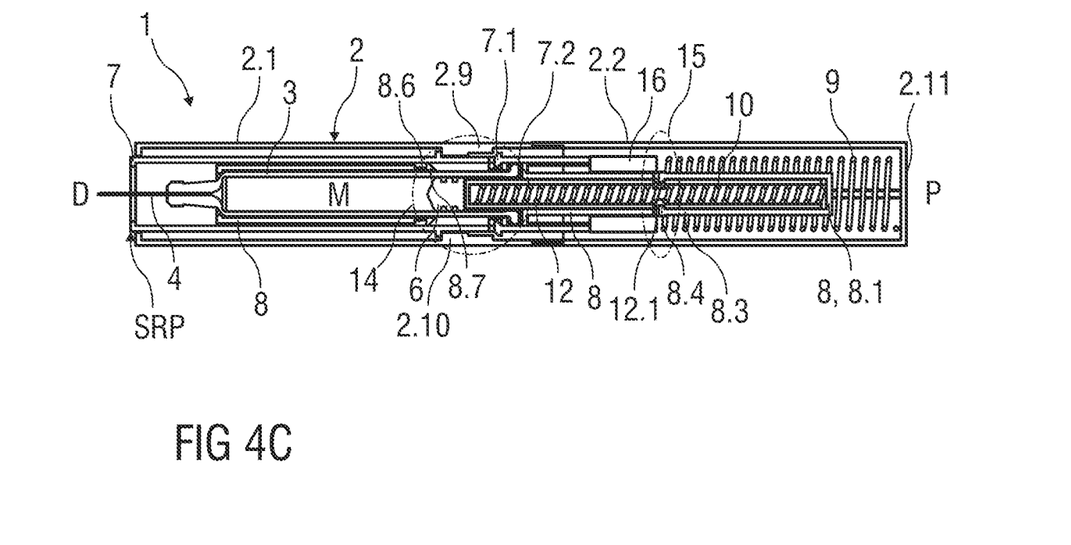
FIG. 4C is a different longitudinal section of an exemplary embodiment of an autoinjector during use.

FIGS. 4A-C are perspective views of the autoinjector 1 being pressed against an injection site. When the shroud boss 7.1 disengages the carrier opening 8.6, the syringe carrier 8 is decoupled from the needle shroud 7. The control spring 9 applies the biasing force to the collar 16, and the collar boss 16.1 pushes the step 8.5 on the syringe carrier 8 to drive the syringe carrier 8 (and the syringe 3) in the distal direction D. When the syringe carrier 8 abuts a front stop 2.8 in the case 2, the needle 4 protrudes beyond the distal end of the case 2 and is inserted into the injection site. The collar 16 has been advanced in the distal direction D to such an extent, that the collar boss 16.1 is no longer supported by the narrow section 2.4 but has reached the wide section 2.5 of the case 2. The control spring 9 continues advancing the collar 16 and due to the syringe carrier 8 having abutted the front stop 2.8, the collar boss 16.1 is deflected radially, disengaging the collar 16 from the syringe carrier 8. The collar 16 advances further under the force of the control spring 9 until it abuts the needle shroud 7.

As the collar 16 advances, it is distal of the first boss 8.4 on the syringe carrier 8 so as to allow radially deflection of the first boss 8.4 due to its ramped engagement to the first opening 12.1 under load from the drive spring 10. The plunger 12 is thus released and advanced by the drive spring 10 displacing the stopper 6 within the syringe 3 and ejecting the medicament M through the needle 4. The release of the plunger release mechanism 15 may provide an audible and/or tactile feedback to the user. The progress of the delivery of the medicament M can be observed through the viewing window 2.7 by examining the movement of the plunger 12. The plunger 12 (which may be a contrasting color to the case 2) is visible in the viewing window 2.7, providing visual feedback about whether or not the autoinjector 1 has been used.

If the user removes the autoinjector 1 from the injection site at any time after the needle 4 having reached insertion depth, the needle shroud 7 moves in the distal direction D, because it is abutted by the collar 16 which is driven by the control spring 9.

Figure 5A:
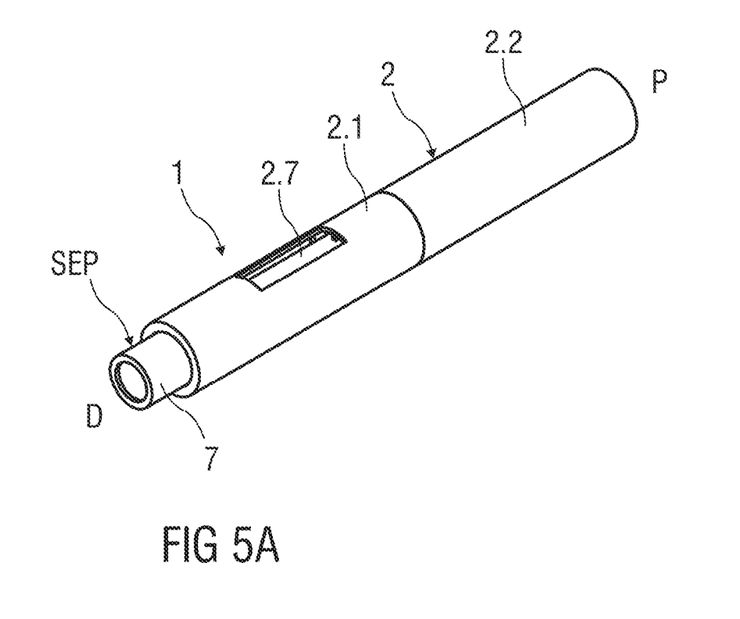
FIG. 5A is a perspective view of an exemplary embodiment of an autoinjector after use.
Figure 5B:
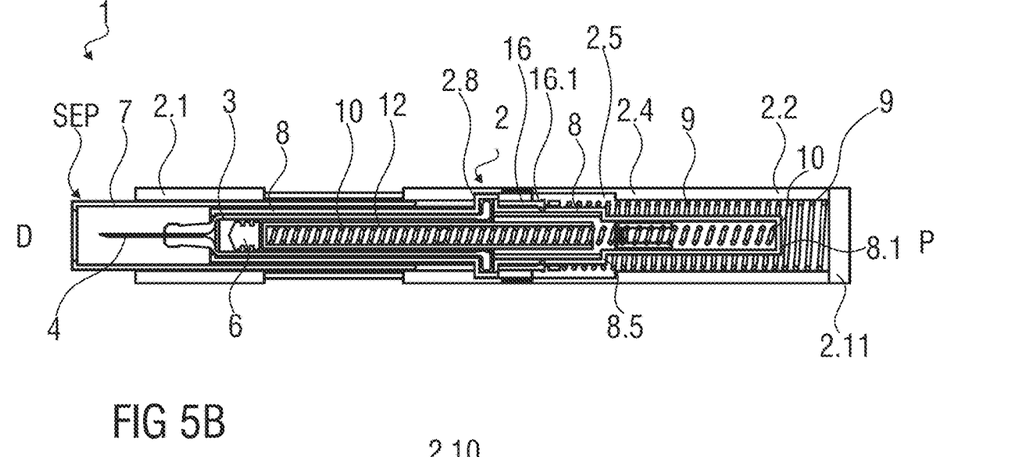
FIG. 5B is a longitudinal section of an exemplary embodiment of an autoinjector after use.
Figure 5C:
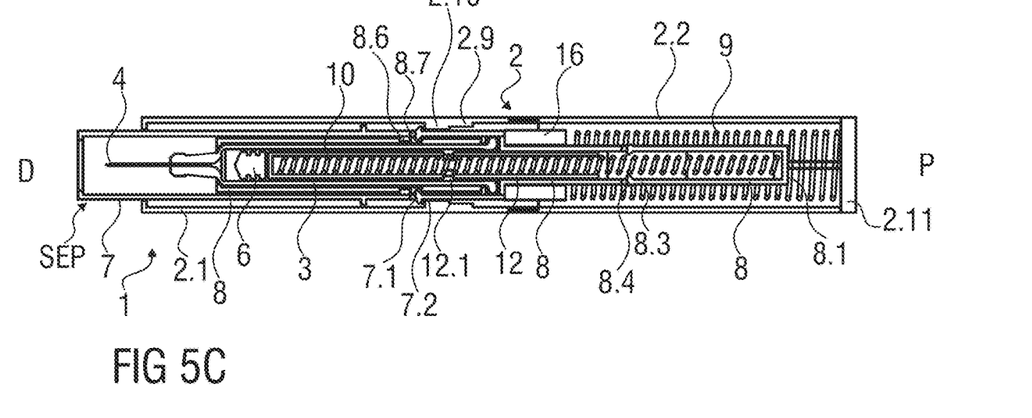
FIG. 5C is a different longitudinal section of an exemplary embodiment of an autoinjector after use.

FIGS. 5A-C are perspective views of the autoinjector 1 after it is removed from the injection site. As the needle shroud 7 advances in the distal direction D under the force of the control spring 9, the shroud boss 7.1 is deflected radially by the axial case boss 2.10 since the syringe carrier 8 has been moved in the distal direction D during needle insertion and does not abut the shroud boss 7.1. The shroud boss 7.1 hence deflects around the case boss 2.10, and then returns to a non-deflected position when it is distal of the case boss 2.10. The shroud boss 7.1 abuts a ramped stop 8.7 on the syringe carrier 8 which resolves the remaining axial force of the control spring 9 and arrests the needle shroud's 7 extension. The needle shroud 7 is now in a second extended position SEP extending further from the case 2 than in the first extended position FEP and the extended needle 4 is hidden from view and finger access within the needle shroud 7.

Any attempt to displace the needle shroud 7 in the proximal direction P relative to the case 2 from the second extended position SEP is prevented, because the shroud boss 7.1 abuts a distal end of the case boss 2.10.

In another exemplary embodiment, an opening may be arranged in the proximal end 2.11 of the case 2 allowing the proximal part 8.1 of the syringe carrier 8 to protrude proximally from the case 2 and serve as a trigger button (not shown). In this exemplary embodiment, the detent mechanism 14 prevents release of the trigger button prior to depression of the needle shroud 7 into the retracted position RP. The needle shroud 7 may be fully depressed into the second retracted position SRP thereby extending the proximal part 8.1 of the syringe carrier 8 from the case 2 which may then be depressed to start an injection. If the trigger button is not depressed at this point, the needle shroud 7 can re-extend into the first extended position FEP and the autoinjector 1 can return to its initial state. If the trigger button is depressed, it may be locked to the case in the depressed position to provide a visual indication that the autoinjector 1 has been used.

After full depression of the needle shroud 7 into the second retracted position SRP, the shroud boss 7.1 is no longer supported by the case boss 2.9. The trigger button, e.g., the proximal end 8.1 of the syringe carrier 8 protruding proximally from the case 2 can now be depressed thereby radially outwardly deflecting the shroud boss 7.1 out of engagement with the carrier opening 8.6 due to their ramped engagement. The syringe carrier 8 is thus decoupled from the needle shroud 7 and the control spring 9, coupled to the syringe carrier 8 through the control mechanism 21, advances the syringe carrier 8 in the distal direction D extending the needle 4 from the case 2 in the distal direction D. The length of the syringe carrier 8 and the case 2 may be such that the proximal end 8.1 of the syringe carrier 8 is flush with the proximal end 2.11 of the case 2 once the needle 4 reaches its insertion depth.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39), des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2, or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An auto-injector comprising:
a case adapted to hold a syringe containing a liquid medicament, a stopper being arranged for sealing the syringe proximally and for displacing the liquid medicament through a needle arranged or received at a distal end of the syringe; and
a needle shroud telescoped within the case and movable between an extended position and a retracted position, the needle shroud biased relative to the case toward the extended position by a control spring, wherein the syringe is held in a syringe carrier, and the syringe carrier is slidably arranged within the case;
wherein the syringe carrier comprises a distal portion adapted to hold the syringe and a proximal portion adapted to retain a plunger,
wherein the auto-injector is configured such that the needle shroud is moved towards the extended position relative to the syringe carrier by the control spring, and
wherein the control spring is proximally grounded in the case by direct physical contact to the case.

2. The auto-injector of claim 1, further comprising a detent mechanism provided to initiate automated needle insertion, wherein the detent mechanism also locks the needle shroud after the auto-injector has been removed from an injection site in the extended position,
wherein the detent mechanism comprises at least one beam on the needle shroud that is configured to interact with the case and with the syringe carrier to initiate automated needle insertion.

3. The auto-injector of claim 2, wherein the beam comprises a resilient shroud beam on the needle shroud having a shroud boss releasably engaging a carrier opening in the syringe carrier.

4. The auto-injector of claim 3, wherein at least one of a surface of the shroud boss or a surface of the carrier opening is ramped to reduce a force necessary to displace the needle shroud from the extended position to the retracted position against a biasing force of the control spring.

5. The auto-injector of claim 3, wherein, when a force on the needle shroud overcomes a biasing force of the control spring, the shroud boss abuts the carrier opening and deflects radially via a shroud beam coupled to the shroud boss, disengaging the needle shroud from the syringe carrier, wherein, when the needle shroud is in a first extended position relative to the case, the shroud boss radially abuts a radial case boss, which prevents the needle shroud from disengaging the syringe carrier when the needle shroud is in the first extended position, wherein an axial case boss is adapted to distally abut the shroud boss such that the needle shroud cannot be moved distally beyond the first extended position prior to use.

6. The auto-injector of claim 5, wherein at least one of a surface of the shroud boss or a surface of the axial case boss is ramped such that if an axial force directed in a distal direction is applied to the needle shroud relative the case, the needle shroud moves in the distal direction relative the case and the shroud boss is radially inwardly deflected via the shroud beam around the axial case boss, wherein, prior to use of the auto-injector, the shroud boss is prevented from deflecting radially inward by a presence of the syringe carrier so that the needle shroud does not disengage the case.

7. The autoinjector of claim 2, wherein the detent mechanism comprises a first engagement surface on the case, a second engagement surface on the case and a third engagement surface on the syringe carrier,
wherein the first engagement surface is arranged proximally relative to the second engagement surface,
wherein the at least one beam is configured to engage the first engagement surface and the third engagement surface to releasably couple the needle shroud to the syringe carrier in a first position of the detent mechanism, and
wherein the at least one beam is configured to engage the second engagement surface to couple the needle shroud to the case in a second position of the detent mechanism.

8. The auto-injector of claim 1, wherein a drive spring is grounded proximally on a proximal end of the syringe carrier and distally on a distal end of the plunger and/or wherein the plunger is telescopically coupled to the proximal portion of the syringe carrier, and the drive spring is arranged within the plunger and biases the plunger distally.

9. The auto-injector of claim 1, further comprising:
a plunger release mechanism arranged for preventing release of the plunger prior to the needle reaching an insertion depth and for releasing the plunger once the needle reaches its insertion depth,
wherein the plunger release mechanism comprises an engagement surface on the syringe carrier and an engagement surface on the plunger, the engagement surface of the syringe carrier configured to engage the engagement surface of the plunger to releasably couple the plunger to the syringe carrier.

10. The auto-injector of claim 9, wherein the plunger release mechanism comprises:
one or more compliant beams with a respective first boss arranged on the syringe carrier, wherein a respective first opening is laterally arranged in the plunger for engaging the respective first boss of the one or more compliant beams,
a collar slidably arranged within the case and over the syringe carrier, wherein, when the needle shroud is in the extended position, the collar abuts the respective first boss of the one or more compliant beams, preventing it from disengaging the respective first opening, wherein, as the needle reaches its insertion depth, the collar moves axially away from the respective first boss of the one or more compliant beams, so that the respective first boss of the one or more compliant beams may deflect via the one or more compliant beams and disengage from the respective first opening and so that the syringe carrier is then disengaged from the plunger.

11. The auto-injector of claim 1, further comprising a control mechanism comprising at least one slidable element arranged on the syringe carrier for selectively coupling the control spring to the syringe carrier or to the needle shroud for advancing either in a distal direction or opposing movement thereof in a proximal direction.

12. The auto-injector of claim 11, wherein the at least one slidable element corresponds to a collar slidably arranged within the case and over the syringe carrier, wherein the collar is a component of the control mechanism.

13. The auto-injector of claim 12, further comprising a detent mechanism provided to initiate automated needle insertion,
wherein the detent mechanism comprises a beam on the needle shroud that is configured to interact with the case and with the syringe carrier to initiate automated needle insertion,
wherein the detent mechanism also locks the needle shroud after the auto-injector has been removed from an injection site in the extended position, wherein, prior to use, the control spring is compressed between the case and the collar, wherein the control mechanism couples the collar to the syringe carrier which is in turn coupled to the case by the detent mechanism.

14. The auto-injector of claim 11, wherein the control spring is proximally grounded in the case and distally bears against the at least one slidable element which is movable axially with respect to the case and arranged over the syringe carrier, wherein the at least one slidable element comprises at least one boss adapted to be engaged to a step in the syringe carrier.

15. The auto-injector of claim 14, wherein, once assembled, the at least one boss is prevented from deflecting radially by a narrow section in the case, wherein a wide section is arranged distally from the narrow section, wherein, upon axial movement of the syringe carrier and the at least one slidable element in the distal direction, the at least one boss can deflect radially when the at least one slidable element enters the wide section and disengage the at least one slidable element from the syringe carrier under a force from the control spring.

* * * * *